United States Patent [19]

McKenna

[11] Patent Number: 5,183,812
[45] Date of Patent: Feb. 2, 1993

[54] PREPARATION AND USE OF THIOPHOSPHONATES AND THIO-ANALOGUES OF PHOSPHONOFORMIC ACID

[76] Inventor: Charles E. McKenna, 16625 Pequeno Pl., Pacific Palisades, Calif. 90272

[21] Appl. No.: 768,155

[22] Filed: Sep. 30, 1991

Related U.S. Application Data

[62] Division of Ser. No. 369,468, Jun. 21, 1989, Pat. No. 5,072,032.

[51] Int. Cl.⁵ .................. A61K 31/66; C07F 9/38; C07F 9/40
[52] U.S. Cl. ............................ 514/120; 558/87; 558/181
[58] Field of Search ................. 514/120; 558/87, 181

[56] References Cited

PUBLICATIONS

Hutchinson, D. W. et al., *IRCS Med. Sci.,* 1986, 14(2), 176–177; *Chem. Abstr.* 1986, 105, 17828.
Thiel, K. D. et al., *Pharmazie* 1986, 41(4), 295–296.
Issleib, K. et al. *Z. Anorg. Allg. Chem.* 1985, 530, 16–28. *Chem. Abstr.* 1985, 103, 196248.
Homer, L. et al., *Phosphorus Sulfur* 1982, 12(2), 259–261; *Chem. Abstr.* 1982, 96, 181354.

*Primary Examiner*—Mary C. Lee
*Assistant Examiner*—Michael G. Ambrose
*Attorney, Agent, or Firm*—Poms, Smith, Lande & Rose

[57] ABSTRACT

Methods for converting phosphonates into thiophosphonates and specific thiophosphonate compounds so produced are disclosed and claimed. The methods start with a reaction mixture formed of a phosphonate compound, including one or more strong electron-withdrawing groups located adjacent to the phosphorus in the compound, a slight excess of Lawesson's reagent, and a polar aprotic solvent. The reaction mixture is heated until reaction is complete and may be followed with separation or hydrolyzation steps to produce thiophosphonic acids and their addition salts. One of these thio-analogues, thiophosphonoformic acid (TPFA) is particularly effective at inhibiting HIV replication and in treating HIV infection.

7 Claims, No Drawings

PREPARATION AND USE OF THIOPHOSPHONATES AND THIO-ANALOGUES OF PHOSPHONOFORMIC ACID

REFERENCE TO EARLIER APPLICATION

The present application is a division of earlier application Ser. No. 369,468, filed Jun. 21, 1989, now U.S. Pat. No. 5,072,032.

BACKGROUND OF THE INVENTION

1. Field of the Invention

The present invention is directed to new and useful processes for the large scale production of thio-analogues of phosphonoformic acid (PFA) and to the conversion of phosphonates into thiophosphonates in general as well as to the thio-PFA (TPFA) compounds produced by these procedures. An additional aspect of the present invention relates to the use of these thio-PFA compounds as antiviral agents which are particularly effective against HIV.

2. Description of the Prior Art

Organic compounds of the general structure

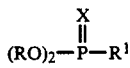

wherein X is oxygen (O) or sulphur (S) are known, respectively, as phosphonates and thiophosphonates. These compounds are implicated in a variety of biological processes and show promise in basic research for medical and agricultural uses including pesticide and antiviral compounds. Unfortunately, research involving thiophosphonates is often hindered by the extreme difficulty in producing even small quantities of these phosphonate analogues. Moreover, economic methods for the large scale production of thiophosphonates are virtually unknown.

For example, of particular interest to the present invention are the thio-analogues of phosphonoformic acid. Phosphonoformic acid (PFA) and its thio-analogue, thiophosphonoformic acid (TPFA) have the following general formulae and structures:

PFA
(HO)₂P(O)COOH
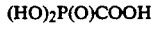
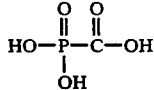

TPFA
(HO)₂P(S)COOH
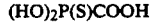
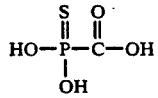

Early efforts reportedly producing TPFA utilized the Michaelis-Becker reaction between the sodio-derivative of diethyl thiophosphite and ethyl chloroformate or chloroacetate, followed by the removal of the P-OEt groups with iodotrimethylsilane (ITMS) at high temperature over 48 hours. However, recent research has indicated that this method is not reproducible and, because of difficulties including the removal of the ethyl groups, produces mixtures of a variety of compounds rather than the desired TPFA. Other proposed methods for the synthesis of TPFA are equally difficult and expensive utilizing numerous steps with exceptionally low product yields. Similar difficulties and expense are associated with the production of the thio-analogues of other phosphonates as well.

Difficulties in producing usable quantities of thiophosphonates are not restricted to commercial applications requiring large quantities of product. Basic research involving these compounds also requires readily available, pure materials. For example, as proposed and claimed by the present invention, TPFA shows great promise as an antiviral agent for use in combatting HIV infection and AIDS in mammals. These properties could not be determined in the past due to the inability of the prior art methods to produce usable quantities of essentially pure TPFA. However, before discussing these antiviral properties in detail, a general understanding of antiviral therapy will be of assistance.

Unlike infectious bacteria, which are functionally and physically distinct and can reproduce outside the cells of their host organisms, the simplicity of viruses makes them able to replicate only by physically invading a host cell and co-opting its biochemical mechanisms to make new viral components. As a result of this intimate connection with the replication cycle of the host cell, viruses present few unique biochemical features which can be selectively attacked without poisoning the host cell. As recently as the 1960's, it was believed that the only strategy for controlling viral infections was the development of vaccines against specific viruses to forestall infection by stimulating the immune system of uninfected individuals in advance.

In spite of these problems, recent developments in the understanding of the details of viral functions have brought to light unique aspects of viral activities which may provide targets for attack. This accumulating body of knowledge has made it possible to identify compounds that may selectively interfere with these viral activities without poisoning the host cells of the infected organism. For example, in both lytic viral infections (those that spread rapidly throughout the population of vulnerable cells, destroying them early in the illness) and persistent viral infections (those that do not always kill an infected cell) the viral agents complete their replication cycles through a number of unique steps that an antiviral drug may interrupt.

Unfortunately, the present state of the art is such that antiviral drugs are only capable of attacking such viruses when they are replicating. Attacking a latent virus such as HIV which does not reproduce itself following infection until reactivated by presently unknown factors would require distinguishing the viral genetic material from the surrounding host genetic material and selectively destroying it. Thus, the current generation of antiviral drugs is only effective against replicating viruses.

Nonetheless, there are notable successes in the field of antiviral drug therapy. An exemplary antiviral compound is acyclovir, a nucleoside analogue which mimics the structure of a precursor of DNA. Acyclovir has been found to interfere with the viral enzymes thymidine kinase and DNA polymerase specific to some herpes viruses, thereby inhibiting the synthesis of the viral DNA and ultimately viral replication itself. Similar antiviral effectiveness has been produced with a different nucleoside analogue, ribavirin which interferes with a viral enzyme crucial to the synthesis of DNA and RNA as well as selectively inhibiting viral mRNA and thus the production of viral proteins. Though far more effective against viral functions, ribavirin, like many antiviral compounds, may also affect human cells and thus may be toxic to rapidly metabolizing cells such as blood cells, limiting its applicability and usefulness.

In spite of these and other antiviral success stories, the most important current challenge for the development of antiviral compounds is the need for an effective treatment against HIV, the viral cause of the AIDS pandemic. In contrast to the bleak epidemiological picture of AIDS wherein potentially millions of people are believed to be infected, the accumulation of knowledge about HIV and its functions has been unprecedentedly rapid. Though only identified in 1983, HIV is known to be a retrovirus whose main target is the T4 lymphocyte, a white blood cell which marshals the immune defenses of the infected host. Additionally, the virus also infects cells in the central nervous system.

After binding to a host cell, HIV penetrates the cell and exposes its viral genetic material: a single strand of RNA. Accompanying the viral RNA is a viral enzyme known as reverse transcriptase which converts the viral genetic material into DNA which becomes integrated into the chromosomes of the infected host cell. The integrated viral genome or "provirus" remains latent until the host cell is stimulated and then directs the synthesis of viral proteins and RNA which assemble to form new HIV particles which burst from and destroy the host cell.

The current target for antiviral drug therapy against HIV replication is the reverse transcription step which is crucial to the viral replication yet irrelevant to the infected host cells. A variety of antiviral drugs have been shown to reduce the activity of HIV reverse transcription in vitro to varying degrees. These compounds include azidothymidine (AZT), suramin, antimoniotungstate, dideoxynucleotides, and phosphonoformate. AZT, has shown significant positive effects in large-scale clinical trials though major concerns remain about its considerable toxicity to bone-marrow cells.

Several researchers have indicated that the pyrophosphate analogues, phosphonacetic acid (PAA) and phosphonoformic acid (PFA) possess antiviral properties in that they inhibit the replication of several viruses including influenza virus A and herpes virus HSV-I. Research has shown that these compounds have an inhibitory activity on the reverse transcriptase of influenza virus A and the DNA polymerase of HSV-I as well as on the DNA polymerase of mammalian cells. (D. W. Hutchinson, G. Semple, and D. M. Thornton, Synthesis and Biochemical Properties of Some Pyrophosphate Analogues, *Biophosphates and Their Analogues—Synthesis, Structure, Metabolism and Activity*, K. S. Bruzik and W. J. Stec (Eds.), Elsevier Science Publishers, B.V., 1987, 441-450.)

Additionally, it has also been suggested in the art that the thio-analogues of phosphonoacetic acid (PAA) and phosphonoformic acid (PFA) may have potential as antiviral agents. (D. W. Hutchinson and S. Masson, The antiviral potential of compounds containing the thiophosphoryl group, I.R.C.S. Medical Science 14 (1986) 176-177.) However, recent research by the inventor has raised significant questions as to the veracity of such reports. It is believed that the reported activities of the alleged thio-PFA compounds discussed in these prior art references are deceivingly incorrect as the proper art methods for preparing these compounds do not produce TPFA but, instead, produce mixtures of different, unidentified compounds.

Moreover, as those skilled in the art will appreciate, further questions as to the accuracy and basis of such unsupported speculation with respect to the proposed properties of TPFA results from the fact that the inhibition of viral enzymes by such compounds in general is uniquely specific to the viral enzymes involved. Thus, it is impossible to predict the antiviral activity of a particular compound as that compound may or may not be effective against a particular virus. For example, acyclovir has proven to be beneficial in infection by Herpes virus, yet acyclovir-resistant strains of Herpes virus have been located. Similarly, Epstein-Barr virus (EBV) is relatively insensitive to acyclovir. Thus, it is clear that early signs of some antiviral activity are not indicative of a compound's effectiveness as an antiviral drug.

Further complicating matters, a compound which may inhibit viral activity may also inhibit critical functions of the host cell and thus prove to be toxic to the host. As a result, antiviral compounds which may be effective in vitro may not be effective as antiviral agents in vivo due to a lack of significant differences in their relative inhibitory activities with respect to viral and host cell mechanisms.

Accordingly, it is a principal object of the present invention to disclose methods for the effective production of large quantities of thio-analogues of PFA in order to facilitate the research and utilization of such compounds.

It is an additional object of the present invention to disclose processes for inexpensively producing large quantities of relatively pure TPFA and its analogues.

It is a further object of the present invention to disclose novel thio-analogues of PFA.

As those skilled in the art will also appreciate, it is also an object of the present invention to disclose novel methods for converting the general class of phosphonate compounds into thiophosphonates in a simple and economical manner.

It is yet another object of the present invention to disclose methods for inhibiting viral and viral enzyme activities, including those of HIV, utilizing TPFA.

Lastly, it is a further additional object of the present invention to disclose methods for treating HIV infection in mammalian cells utilizing TPFA or its addition salts as effective antiviral compounds.

SUMMARY OF THE INVENTION

Generally stated, the present invention accomplishes the above-described objectives by providing methods for readily converting phosphonates such as PFA into thiophosphonate analogues such as trimethyl-TPFA in a single step reaction which provides unusually high product yields. Moreover, following hydrolysis the TPFA and TPFA analogues produced through the methods of the present invention have unexpectedly high antiviral activities against HIV while exhibiting unexpectedly low DNA polymerase inhibiting activity against mammalian enzymes making them particularly well suited for use as effective anti-HIV agents.

What is more, the processes of the present invention have wide applicability in converting phosphonates into thiophosphonates for the economical production of a wide variety of compounds including insecticides incorporating thiophosphonate units. Because the methods of the present invention produce desirable thio-analogues of phosphonates with a synthesis that is short, simple, efficient and which utilizes inexpensive starting materials, the present invention also produces such compounds in large quantity at relatively low cost.

More particularly, the methods of the present invention convert phosphonates of the general formula:

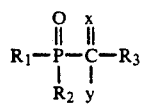

where $R_1$, $R_2$, and $R_3$ when present as substituents are each independently hydrogen, hydroxy, methyl, alkyl, aryl, saturated, unsaturated, substituted or unsubstituted organic compounds, through the following steps.

First, the phosphonate is modified by substituting one or more strong electron withdrawing groups such as a halogen or doubly-bonded oxygen for x and y on the alpha carbon adjacent to the phosphorus in the general formula. Those skilled in the art will appreciate that it is unnecessary to modify phosphonate compounds in accordance with the teachings of the present invention where the alpha carbon is already bonded to a sufficiently strong electron withdrawing group. It should be noted that, without limiting the scope of the present invention, it is believed that the electron withdrawing group or groups must be directly adjacent to the phosphorus atom of the molecule in order for the reaction to proceed and must be sufficiently strong to drive the following unexpected reaction sequence.

The next phase of the method of the present invention involves forming a reaction mixture of the modified phosphonate, an effective amount of one or more forms of Lawesson's reagent (for example, approximately one equivalent of a dimer of P-methoxyphenylthionophosphine sulfide or other suitable phosphetane ring containing compounds) and polar, aprotic solvent. An exemplary solvent is acetonitrile or toluene, though those skilled in the art will appreciate that any suitable polar aprotic solvent may be utilized. Following the formation of the reaction mixture the mixture is heated until conversion of the phosphonate into its thiophosphonate analogue is substantially complete.

Preferably, the heating will take place under an inert, anhydrous atmosphere to prevent interference with the conversion reaction. Exemplary heating temperatures can range from approximately 66° C. to 110° C. depending on the solvent utilized and may include reflex conditions. Additionally, heating times may be 1 hour or less, though preferably will be on the order of 2 to 6 hours. In practice, upon heating the reaction mixture, the Lawesson's reagent will be observed to gradually disappear and dissolve into the mixture conveniently signaling that the reaction is progressing to completion.

Once reaction is substantially complete, if desired, the reaction product can be separated from the reaction mixture in a variety of manners. For example, the solvent can be evaporated and any side product (for example modified Lawesson's reagent, a trimer of P-methoxyphenylthionophosphine oxide) can be precipitated out of the solution. Conversely, it is possible to distill the thiophosphonate analogue from the mixture directly. Using the foregoing methodology and distilling the product directly from the reaction mixture will produce a pure product with yields up to and possibly exceeding 87%. In that the reagents utilized for this essentially one-step reaction are relatively inexpensive, and the yields of pure product are so high, the economies of the present invention become readily apparent.

An exemplary phosphonate conversion in accordance with the teachings of the present invention utilizes trimethyl phosphonoformate as a starting material to produce trimethyl thiophosphonoformate (O,O-dimethyl carboxymethylphosphonothioate). The trimethyl phosphonoformate is mixed with approximately one equivalent ($\pm 2$-5%), of Lawesson's reagent in a generally two-to-one stoichiometric relationship such that there are two moles of trimethyl phosphonoformate for every mole of Lawesson's reagent. The aprotic, polar solvent used is, preferably, either acetonitrile or toluene and the mixture is heated under argon for two to six hours at a preferred temperature of 82° C. for acetonitrile until the Lawesson's reagent is observed to dissolve into the mixture.

The trimethyl thiophosphonoformate so produced may be separated from the reaction mixture if desired through precipitation or distillation and, in accordance with the teachings of the present invention, may be further modified through hydrolysis to produce thiophosphonoformic acid (TPFA) and its addition salts. Preferably, when desired, hydrolysis will take place under basic conditions such as the utilization of sodium hydroxide (NaOH) to directly hydrolyze the trimethyl-TPFA to TPFA. Conversely, though ITMS-H$_2$O will not hydrolyze the ethyl-ester of TPFA, it was surprisingly discovered to be effective at hydrolysing the methyl ester.

The TPFA so produced may then be utilized in accordance with the teachings of the present invention as a antiviral inhibitor against HIV virus and in a method for treating mammals infected with HIV. As will be discussed in detail below, this unique and unexpected antiviral activity against HIV is a product of the high therapeutic index of this compound with respect to HIV. More specifically, recent studies made possible by the method of the present invention show TPFA to be surprisingly effective at inhibiting HIV and HIV reverse transcriptase while being surprisingly less toxic with respect to inhibition of mammalian DNA polymerase.

Moreover, as will be appreciated by those skilled in the art, the conversion of PFA to TPFA gives the sulfur analogue a lower polarity thus providing enhanced cell-penetration and higher water solubility. As a result, it is believed that the TPFA antiviral compounds of the present invention will be significantly less toxic than PFA in treating mammalian cases of HIV infection and inhibit HIV in general.

The above discussed and many other features and attendant advantages of the present invention will become apparent to those skilled in the art from a consideration of the following detailed description.

DETAILED DESCRIPTION OF THE INVENTION

In a broad aspect, the methods of the present invention are based upon two surprising discoveries. First, while it is known in the art that Lawesson's reagent (LR) is effective at converting oxygen to sulfur in carbonyl groups such as those found in ketones or in converting phosphites to thio-phosphites, it was completely unexpected that LR would prove to be so effective at converting phosphonates to thiophosphonates in accordance with the techniques of the present invention. Secondly, the large quantities of pure TPFA so produced made it possible to determine the relatively high therapeutic index of TPFA with respect to the inhibition of HIV versus mammalian enzymes; a result which was also completely unexpected in view of the teachings of the prior art. Thus, the methods of the present invention provide new, uniquely effective procedures for rapidly, simply, and inexpensively producing large quantities of essentially pure thiophosphonates. Of equal or greater significance, the methods of the present invention makes it possible to efficiently produce TPFA and other thio-analogues of PFA in sufficient purity and quantity for use as new, effective antiviral agents against HIV.

Turning first to the general process of converting phosphonates into their thiophosphonate analogues and additions salts thereof, a more detailed understanding of the limitations of the prior art methodologies for producing such compounds is in order. The most widely-known method in the art for reportedly synthesizing thiophosphonates is that currently reported by Hutchinson (D. W. Hutchinson and Masson, The antiviral potential of compounds containing the thiophosphoryl group, I.R.C.S. Medical Science, 14 (1986)176–177). Briefly, Hutchinson, et al, report the preparation of alkylthiophosphonate intermediate compounds utilizing the Michaelis-Becker reaction followed by removal of the alkyl groups utilizing iodotrimethylsilane (ITMS). Generally stated, the prior art Hutchinson et al. reaction mechanics are reported as follows:

1) Michaelis-Becker reaction:

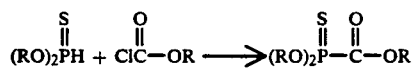

2) Followed by reaction with ITMS:

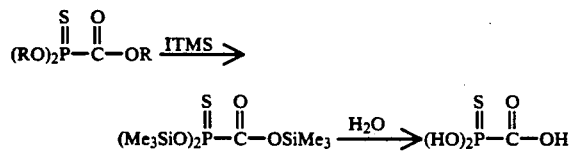

Additionally, a more limited, alternative prior art synthesis of TPFA was proposed in a verbal presentation by Dr. William Egan. Though few details are available on this proposed synthesis, it is believed to include at least eight to ten steps and may require unique and expensive starting materials. Thus, as will be appreciated by those skilled in the art, any such synthesis would be a very long, complicated and expensive process having very low overall product yields.

Similarly, the synthesis proposed by Hutchinson et al. is not without its own problems. In addition to very low yields, the proposed reaction is incomplete and produces mixtures of unidentified products. Though apparently successful at producing some of the intermediate tri-ester compounds, the Hutchinson et al. method apparently is not successful at ultimately removing the alkyl groups with ITMS. Elaboration of these distinguishing features of the prior art methodology will be provided following a more detailed explanation and understanding of the present invention.

As discussed in the foregoing summary section it is known in the art that Lawesson's reagent (LR) will convert doubly-bonded oxygen to sulfur on carbonyl groups such as those in ketones and will convert phosphites into thio-phosphites. There the relative bond energies drive the reaction to completion. However, in the case of phosphonates where oxygen is doubly-bonded to phosphorus the favorable bond energies are not present to drive the reaction as LR also includes phosphorus double bonds. Nevertheless, as disclosed by the present invention, it was surprisingly discovered that LR would successfully convert phosphonates into their thiophosphonate analogues if a sufficiently strong electron-withdrawing group was located adjacent to the phosphorus in the phosphonate as evidenced by the following non-limiting experimental reactions.

All reactions were performed in scrupulously dried glassware under $N_2$. Lawesson's reagent (LR) and Me$_3$PFA were used without purification: CH$_3$CH was distilled from CaH$_2$ under $N_2$. All reactions were performed in acetonitrile unless otherwise noted.

REACTION BETWEEN ME$_3$PFA AND LR 1.66 g (4.11 mmol) LR and 1.38 g (8.22 mmol) Me$_3$PFA were suspended in 25 ml CH$_3$CN and stirred for 2 hours with no apparent reaction. After 12 hours, still no reaction had occurred. After heating for 2 hours, the LR dissolved, and NMR indicated that reaction had occurred. Major product, $^{31}$P NMR: $\delta = 64$ ppm, and $^{13}$C NMR indicated that the ester group was intact. Impurities in the $^{31}$P NMR spectrum could be removed by evaporating the mixture, and extracting residue between saturated aq. NaHCO$_3$ and ether, with the product found in the organic layer. In a reaction between 1 g ester and 1.3 g LR in refluxing THF for 2 hours, NMR suggested that partial reaction had occurred.

REACTION BETWEEN (TMSO)$_2$P(O)CO$_2$ME AND LR 0.5 g ester and 0.35 g LR were reacted as above for 24 hours; $^{31}$P NMR suggested that reaction had occurred: $\delta = 46$ ppm, with impurities. The same reaction was performed with 0.5 g ester and 0.7 g LR, and the same product was obtained in a cleaner reaction. Thus, the reaction was repeated using 6.5 g ester and 6 g LR, and proton-coupled $^{31}$P NMR showed that the phosphorus was coupled to a methyl group. (q, $J$PH - 11 Hz.) CN$^-$ test was negative. Evaporation of the mixture was done: attempted Kugelrohr distillation failed.

REACTION BETWEEN LR AND OTHER SUBSTRATES

Further experiments conducted as above indicated that LR was inert to Et$_3$PFA, Et$_3$FPAA, 1PR$_4$MDP, 1PR$_4$N$_2$MDP under the foregoing conditions. However, slight reaction occurred with Et$_3$F$_2$PAA indicating that substituting strong electron-withdrawing groups such as fluorine adjacent to the phosphorus in the phosphonate compound would drive the reaction to the point that LR would be successful at converting such modified compounds into their thiophosphonate analogues. However, it should be noted that decomposition took place with dibromo and monobromo compounds under the above conditions.

Further demonstrating the utility of the present invention, a variety of experiments were conducted utilizing trimethyl phosphonoformate (Me$_3$PFA) as a starting material for use in accordance with the teachings of the present invention. Those skilled in the art will appreciate that Me$_3$PFA incorporates a strongly electron-withdrawing doubly bonded oxygen directly adjacent to the phosphorus in the compound which, in accordance with the present invention, will enable the thioconversion reaction to proceed utilizing LR. The following non-limiting experiments were conducted utilizing larger amounts of reagents and under varying conditions to further illustrate the scope of the present invention.

GENERAL EXPERIMENTAL PROTOCOL

All glassware was scrupulously oven- or flame-dried. All reactions were performed under dry, pre-purified argon (passed successively through columns of drierite; activated Linde Type 4A molecular sieves; and BASF catalyst). Lawesson's reagent (LR) was purchased from Aldrich Chemical Company (97%) and was used without further purification. Trimethyl phosphonoformate (Me$_3$PFA) was also purchased from Aldrich Chemical Company and was purified by vacuum distillation prior to use (60° C., 15 μm).

Solvents were purified using standard methods. Acetonitrile was distilled from P$_2$O$_5$, then from CaH$_2$; tetrahydrofuran was distilled from benezophenone/sodium ketal, then from lithium aluminum hydride; toluene was distilled from benezophenone/sodium ketal. Hexane and ethyl acetate for chromatography were reagent grade and were used directly. Reactions were monitored by thin layer chromatography using silica gel 60F-254 (Kieselgel) and detected by an ultraviolet lamp (Mineralight UVS-12). Flash column chromatography was performed as described in the literature (Still, W. C.; Kahn, M.; Mitka, A. J. Org. Chem., 1978, 43, 2923.)

NMR spectra were obtained on a Bruker IBM WP-270SY spectrometer operated at frequencies of 270.02 MHz ($^1$H), 109.35 MHz ($^{31}$P) and 67.92 MHz ($^{13}$C). NMR spectra for isolated compounds were obtained in 5 mm tubes using 10% solutions (CDCl$_3$ for esters, D$_2$O for salts). Chemical shifts are reported relative to TMS ($^1$H: internal CHCl$_3$, δ=7.24 ppm; $^{13}$C: using internal CDCL$_3$, δ=77.0 ppm); or external 85% H$_3$PO$_4$ ($^{31}$P). Vacuum distillations were performed on a vacuum line equipped with an all glass oil diffusion pump; pressures were measured on a MacLeod gauge.

Infrared spectra of esters were obtained on a Perkin-Elmer 281 infrared spectrophotometer. Neat samples were run as thin films between NaCl plates. Spectra of salts were taken measured on a FT-IR/32, infrared spectrophotometer.

High resolution mass spectra were obtained at the Mass Spectral Facility, University of California, Riverside, Calif.

Elemental analyses were performed by Galbraith Laboratories, Knoxville, Tenn.

EXPERIMENT 1

A 500 mL three-necked round-bottomed flash equipped with reflux condenser, magnetic stirrer and thermometer was connected to an Ar bubbler, flushed with Ar and charged with 375 mL acetonitrile. Me$_3$PFA (22.0 g, 130.9 mmol) was added (syringe) and dissolved (magnetic stirring). Lawesson's reagent (LR) (dimer of p-methoxyphenylthionophosphine sulfide) (26.40 g, 65.45 mmol) was added as a pale yellow, chalky powder to the flask (glove bag, Ar). After stirring for 2 h at room temperature, no reaction or solubilization was evident. The mixture was then refluxed at 82° C. for 6 h, during which time the LR appeared to gradually dissolve, giving a dark-yellow solution. The reaction mixture was cooled to room temperature causing precipitation of a creamy white powder. This was removed by suction filtration (9.186 g, fluted filter paper, Eatman Diechmann Grade 515, 12.5 cm) giving a pale yellow solution which was washed and filtered three times with 20 mL diethyl ether. Excess ether and acetonitrile were removed by evaporation, leaving a pale yellow oil, whose $^{31}$P NMR ($^1$H) showed signals at δ=71.9–83.8 ppm and at δ=65 ppm(s); no signal was observed at δ=2 ppm (trimethyl PFA). After 1 day at room temperature, a white crystalline solid precipitated from the crude residue. TLC analysis of the supernatant (TLC - I), (hexane:ethyl acetate, 6:1) revealed a single migrating spot at R$_f$ 0.35, in addition to a spot at the sample origin. The following summary of analytical TLC results (TLC - II) evaluating different solvents were performed using silica gel 60F (Eastman Chromagram), detected by an ultraviolet lamp. In all cases, the mixture resolved into two very intense blue mobile spots with no detection of Me$_3$PFA present. In a comparison between Me$_3$PFA (R$_f$ 0.06) and Me$_3$TPFA (R$_f$ 0.35), the latter was much more intense under ultraviolet detection. TLC (hexane:EtOAC, 7:3): Rf 0.07, 0.62, 0.81. (hexane): too weak. (ether): R$_5$ 0.66, 0.10. (chloroform): no separation. EtOAC: R$_f$ 0.10, 0.90. (methylene chloride): R$_f$ 0.06, 0.64, 0.90, no strong separation.

The reaction mixture (29 g of total 44 g of crude product) was separated by flash column chromatography (TLC - I, same solvent system). Like fractions (TLC) were combined and evaporated to yield ($^{31}$P NMR) virtually pure Me$_3$TPFA (0,0-Dimethyl Carboxymethylphosphonothioate) (13.29 g), (contained a trace of impurity with δ=72 ppm). Pure product was obtained by fractional distillation in vacuo: very pale mobile oil, bp 37°–39° C. (10 μm), 10.83 g (87% yield).

More conveniently, the crude supernatant (10 g of 44 g crude product) was directly distilled, giving 4.75 g (87% yield) distillate, pure by TLC, IR, $^{31}$P and $^1$H NMR. Bp: 37°–39° C., (10 μm). TLC (hexane:EtOAC, 6:1): R$_f$ 0.35. $^1$H NMR: δ=3.81 ppm (d, $^3$J$_{PH}$=14 Hz, C(O)OCH$_3$); 3.85 ppm (d, $^3$J$_{PH}$=1 Hz, P(S)OCH$_3$). $^{13}$C NMR: δ=54.3 ppm (qd, $^1$J$_{CH}$=150 Hz, $^3$J$_{CP}$=7 Hz, CH$_3$); δ=52.7 ppm (qd, $^1$J$_{CP}$=149 Hz, $^3$J$_{CP}$=5 Hz). $^{31}$P NMR: δ=64.8 ppm (septet, $^3$J$_{PH}$=14 Hz). IR: 1722 cm$^{-1}$ (s, v$_{co}$), 1035 cm$^{-1}$ (m, $^v$POC) no peak at 1290 cm$^{-1}$ (V$_{PO}$, Me$_3$PFA). MS: Parent ion m/e 1984, major fragments m/e 125 [(CH$_3$O)$_2$PS$^+$], m/e 93,79. Parent ion m/e calculated: 183.9959; Found; 183,9956. Anal. calculated for C$_4$H$_9$O$_4$PS: C, 26.09; H, 4.93; S, 17.41. Found: C, 26.23; H, 5.00; S, 17.82.

It was shown by TLC that the second fraction collected from flash column chromatography (R$_f$ 0.14) upon evaporation crystallized from hexane: EtOAC, 4:1. These crystals were very soluble in chloroform and had the same R$_f$ values as the creamy white precipitate that came out of solution and the crystalline solid found on the bottom of the crude flask. IR and NMR spectra indicate aromatic rings present. A white diamond-shaped crystal suited for x-ray diffraction crystallography was mounted on a 0.3 mm glass capillary. Data was collected on a four-circle-Nicolet/Syntex P$_{21}$ diffractometer employing Cuα radiation. A large triclinic cell with a volume of 2438 A$^3$ was revealed by carefully machine-centering fifteen strong reflections, a procedure which also yielded the orientation matrix needed for data collection. The crystal data is currently being solved. $^{31}$P NMR: δ~7 ppm. $^1$H NMR: δ=72 ppm (m).

Attempts to remove byproducts by extractions between saturated aqueous NaHCO$_3$ and ether were unsuccessful.

EXPERIMENT 2

The same reaction was repeated under identical conditions. LR gradually went into solution and the reaction was refluxed at 82° C. for 6 h. However, upon cooling to room temperature quickly followed by evaporation of acetonitrile, no precipitation was seen. The reaction mixture (57.7 g) was separated by flash column chromatography (TLC - I, solvent system) with 10–12 g of crude residue loaded per column. One column was done with Aldrich silica gel (TLC standard grade, 2–25μ). Routine TCL - I analysis indicated that in addition to Me$_3$TPFA (R$_f$ 0.36), another non polar intense blue spot was observed (R$_f$ 0.46). Like fractions and fractions with mixtures of these two spots were combined, evaporated and vacuum distilled (bp 38.5° C., 10 μm) yielding Me$_3$TPFA contaminated with impurities (7.84 g, 33% yield). $^{31}$P NMR ($^1$H) of the distillate indicated only pure Me$_3$TPFA (δ=64.8 ppm) however TLC analysis still showed two spots. A further TLC - I analysis of the impurity (R$_f$ 0.56) was made by varying the amount of sample spotted on the plate. The plate was observed under an ultraviolet lamp and then treated with phosphomolybdic acid (spray, 7% solution in ethanol). Examination of the TLC plate revealed that this compound consisted of a light blue spot (R$_f$ 0.56) in addition to a dark violet-blue spot (R$_f$ 0.39), the latter of which has a similar R$_f$ value to Me$_3$TPFA (R$_f$ 0.35) which appeared to be a faint blue color. $^{31}$P NMR ($^1$H) showed a signal at δ=99.99 ppm. This impurity was carefully removed by flash column chromatography. (TLC - I, solvent system). A long column vacuum distillation yielded pure Me$_3$TPFA (6.50 g, 27% yield, bp 39.5° C., 10 μm).

EXPERIMENT 3

Several reactions were run changing the reactants addition order. In a 100 mL round-bottomed flask, LR (5.3 g, 13.09 mmol) was added under Ar and charged with 75 mL acetonitrile (glove bag, Ar). No immediate reaction or solubilization was evident with stirring. Me$_3$PFA (4.4 g, 26.18 mmol) was added (syringe) and the mixture was refluxed at 82° C. for 6 h at which time LR appeared to gradually dissolve giving a dark yellow solution. When the reaction mixture was cooled to room temperature, no precipitation was seen. Only after evaporation of acetonitrile, a crystalline solid precipitated from the crude residue which was identical to the solid described in the experiment previously (TLC - I). Flash column chromatography (TLC - I, solvent system) and vacuum distillation yielded pure product, Me$_3$TPFA (2.78 g, 57% yield).

EXPERIMENT 4

In a similar reaction, LR (5.3 g, 13.09 mmol) was added under Ar and charged with 75 mL THF (glove bag, Ar). Again, no immediate reaction or solubilization was evident with stirring. Me$_3$PFA (4.4 g, 26.18 mmol) was added (syringe) and the mixture was refluxed at 66° C. LR went into solution within 2 h. Refluxing was continued for 4 h more. NMR indicated no starting material left. Again, the crystalline solid precipitated after 1 day standing at room temperature. Pure product was obtained after flash column chromatography (TLC - I, solvent system) and distillation in vacuo, Me$_3$TPFA (2.20 g, 48% yield).

EXPERIMENT 5

In a similar reaction, excess LR (22.62 g, 55.03 mmol) was added under AR to a 500 mL round-bottomed flask and charged with 375 mL acetonitrile (glove bag, Ar). Again, no immediate reaction or solubilization was evident with stirring. Me$_3$PFA (17.56 g, 104.4 mmol) was added (syringe) and the mixture refluxed at 82° C. for 6 h at which time the LR appeared to gradually dissolve giving a yellow solution. The reaction mixture was cooled to room temperature and excess acetonitrile was removed by evaporation leaving a pale yellow oil with slight precipitation of a creamy white powder. After one day standing at room temperature, a large amount precipitated (39.00 g) containing a small amount of yellow oil. The oil was found to be very soluble in hot hexane leaving the solid residue behind. To the crude residue, 200 mL hexane was added and heated with steam until reflux and gravity filtered while hot (steam filtration, Whatman filter paper Grade #1). Excess hexane was removed by evaporation giving a pale yellow oil (13.48 g). TLC analysis of the yellow oil (hexane:ETOAC, 4:1) revealed intense blue spots (R$_f$ 0.46, 0.26, 0.04) under an ultraviolet lamp. Analysis of the precipitate showed two intense blue spots (R$_f$ 0.2, 0.04) and two spots which were lighter blue (R$_f$ 0.56, 0.44). Direct distillation of the crude yellow oil gave 11.63 g (61% yield) distillate (bp 38°–39° C., 10 μm). TLC and $^{31}$P NMR revealed this to be Me$_3$TPFA (δ=64.8 ppm) with a little Me$_3$PFA starting material (6%). The crude residue left in the pot was a thick lemon yellow gum (bp > 100° C.) having the same properties as the LR side product discussed earlier (TLC).

EXPERIMENT 6

Three reactions were performed simultaneously using toluene as the solvent varying the relative amounts of LR used. A 100 mL, and two 250 mL round-bottomed flasks were flushed with Ar and charged with 75 mL toluene. To each flask, Me$_3$PFA (4.4 g, 26.18 mmol) was added (syringe) and dissolved (magnetic stirring). Consecutively, LR (5.6 g, 13.72 mmol) was added to the 100 mL flask (I), LR (11.1 g, 27.4 mmol) was added to one 250 mL flask (II), and LR (16.7 g, 41.2 mmol) was added to the other 250 mL flask (III), (glove bag, Ar). Again, no immediate reaction or solubilization was evident with stirring. The mixtures were refluxed at 100° C. and LR gradually dissolved giving yellow solutions.

All reactions were stopped after 1 h. I was a pale yellow solution with no precipitate present even after cooling to room temperature (similar to the THF reaction). II was a clarified lemon-yellow solution which precipitated a pale yellow crystalline residue at room temperature. III was a darker lemon-yellow solution with a large amount of lemon-yellow precipitate. A summary of TLC results (hexane:ETOAC, 7:3) monitoring the reactions were detected by an ultraviolet lamp. I showed very little of both Me$_3$PFA (R$_f$ 0.08) and Me$_3$TPFA (R$_f$ 0.5) but an intense blue spot similar to the LR crystalline side product previously described (R$_f$ 0.32). II and III showed similar results, however, more Me$_3$PFA was present for these two, I, II and III had similar $^{31}$P NMR ($^1$H) showing signals for Me$_3$TPFA δ=65 ppm(s) and signals at δ=4, 71.8–75.1, and 92.3 ppm.

Refluxing was continued for 1 h and after standing at room temperature overnight I was a pale yellow solution, II was a clarified lemon-yellow solution with a pale yellow crystalline residue and III was a darker clarified lemon-yellow solution with a large amount of crystalline precipitate. TLC analysis (hexane:ETOAC, 7:3) showed an intense blue spot for all three ($R_f$ 0.34) similar to the LR crystalline side product, a light blue spot ($R_f$ 0.56) similar to Me$_3$TPFA, in addition to two light blue nonpolar spots ($R_f$ 0.62, 0.96). Both II and III still showed some Me$_3$PFA present ($R_f$ 0.5). $^{31}$P NMR ($^1$H) of I, II and III revealed the peaks at $\delta > 71$ ppm. Analysis of I showed the singlet at $\delta = 65$ ppm now was a multiplet ($\delta = 65.4$–65.6 ppm). Similarly, analysis of II showed a doublet ($\delta = 65.3$–65.4 ppm). III showed no change ($\delta = 65.5$ ppm).

From the foregoing experiments, it will be apparent to those skilled in the art that the methods of the present invention are particularly effective at producing the thio analogue of Me$_3$PFA, namely trimethyl thiophosphonoformate (O,O-Dimethyl Carboxymethylphosphonothioate). Moreover, the methods of the present invention produce this compound with exceedingly high yields in a very simply, essentially one-step reaction utilizing inexpensive starting materials. As detailed above, the trimethyl thiophosphonoformate can be readily separated from the reaction mixture through distillation or precipitation or chromatographic methodologies.

It is also contemplated as being within the scope of the present invention to utilize the additional step of hydrolyzing the trimethyl thiophosphonoformate to produce thiophosphonoformic acid and/or its addition sales. Preferably, hydrolyzation will take place under basic conditions as illustrated by the following non-limiting examples detailing the production of TPFA and its sodium addition salt. However, those skilled in the art will appreciate that other hydrolyzation methods including the correct usage of ITMS are contemplated as being within the scope of the present invention.

EXPERIMENT 7

2.75 ml of 10N sodium hydroxide solution were added to 1.0 g (5.43 mmol) of Me$_3$TPFA with vigorous stirring at room temperature. After 3–5 minutes, the mixture became hot and the methanol produced evaporated. Stirring was continued for ca. 15 min, and the mixture cooled in an ice bath. The pH was adjusted to 10.5 with 1N HCl. The solvent was evaporated by dry-ice freeze pumping. Distilled water (2 mL) and excess methanol were added. The precipitate formed was centrifuged and over-dried in vacuo, neutralized to pH 6 with 1N HCl then readjusted to pH 10.5 with 1N NaOH. The solvent was again evaporated by dry-ice freeze pumping. Then 1.5 ml water and excess methanol were added. The precipitate formed was centrifuged and oven-dried in vacuo. The process was repeated. 207.5 mg of pure desired salt were obtained (18.4% yield). $^{31}$P NMR: $\delta = 37.7$ ppm (s). $^1$H NMR: $\delta = 4.63$ ppm (H$_2$O) in D$_2$O. $^{13}$C NMR: $\delta = 183.2$ ppm (d, $^1J_{CP} = 181$ Hz, CO). IR. Anal. Calculated for: C, 5.77; H, 0.00; S, 15.41. Found: C, 5.83; H, 0.12; S, 14.91.

Those skilled in the art will appreciate that while the cleavage of ester compounds through basic hydrolysis is known in the art, whether or not a particular di-functional ester will be cleaved under such conditions cannot be predetermined. Thus, as further evidence of the scope of the present invention, it is possible to substitute the di-ethyl ester of TPFA for Me$_3$TPFA in the above experiment to produce TPFA. As expected, when utilizing Et$_3$TPFA as a starting material, some of the foregoing reaction conditions for base hydrolysis must be changed. For example, the reaction time must be increased to approximately thirty minutes and it is also anticipated that the production of side products may be increased.

EXPERIMENT 8

An improved yield of pure Na$_3$TPFA was obtained utilizing the following protocol. As before 2.75 ml of 10N sodium hydroxide solution were added to 1.0 g (5.43 mmol) of Me$_3$TPFA with vigorous stirring at room temperature. After 3–5 minutes, the mixture become hot and cloudy, and most of the methanol produced evaporated. Stirring was continued for approximately 10 min., and the mixture was cooled in an ice bath. Distilled water (3 mL) and 30 mL methanol were added. The precipitate formed was centrifuged and oven-dried in vacuo ($<1$ mm Hg, 50° C.) 10 min., neutralized to pH 4.5 to remove CO$_2$ (from Na$_2$CO$_3$ formed during the reaction), with 3N HCl (approximately 4–5 mL) then readjusted to pH 10.5 with 3N NaOH (approximately 0.5 mL). The solvent was evaporated by lyophilization. Water (2.5 mL) and methanol (30 mL) were then added. The precipitate formed was centrifuged as before and oven-dried in vacuo ($<1$ mm Hg 55° C. for 6 h). The process was repeated. 231.5 mg of pure Na$_3$TPFA (white powder) was obtained (20.5% yield). $^{31}$P NMR: $\delta = 37.7$ ppm (s). $^1$H NMR: no resonances other than HDO. $^{13}$C NMR: $\delta = 183.2$ ppm (d, $^1J_{CP} = 181$ Hz, CO). IR: 1680 cm$^{-1}$ (m), 1095 cm$^{-1}$ (shoulder), 1580 cm$^{-1}$ (s), 1375 cm$^{-1}$ (s), 1140 cm$^{-1}$ (s), 1030 cm$^{-1}$ (s). UV: $\epsilon 254$ nm $= 1.05 \times 10^3$, $\epsilon 233 = 2.44 \times 10^3$, $\epsilon 205 = 6.0 \times 10^3$. Analytical calculated for Na$_3$TPFA: C, 5.77; H, 0.00; S, 15.41. Found: C, 5.83; H, 0.12; S, 14.91.

It should be noted that by using Et$_3$TPFA as starting material, the same product can be obtained, but in low yield and accompanied by impurities. Additionally, when using Et$_3$TPFA as a starting material the reaction time needed to be increased to approximately 30 minutes, resulting in increased formation of side product.

Nonetheless, as will be appreciated by those skilled in the art, the reagents utilized in the foregoing basic hydrolysis experiments are very inexpensive relative to compounds such as ITMS, further contributing to the superior economics of the methods of the present invention. Moreover, as detailed in the following examples, the prior art methodologies utilizing expensive reagents such as ITMS are not successful at producing thiophosphonates such as TPFA.

In the following examples, a variety of phosphonate starting materials were synthesized utilizing either the method of the present invention or that of Hutchinson et al. where possible. These compounds were then subjected to ITMS hydrolysis as disclosed in the prior art to illustrate the difficulties of this prior art methodology and to further distinguish the novel methods of the present invention.

PREPARATION OF O,O-DIETHYL HYDROGEN PHOSPHOROTHIOIITE [EtO)$_2$P(S)H](MICHAELIS-BECKER REACTION)

A mixture of diethyl dithiophosphate and triphenylphosphine was stirred vigorously at 65° C. for 7 h. After fractional distillation in vacuo, the product was obtained in 59% yield, Bp: 61°–62° C. (4 mm). $^{31}$P NMR:

$\delta = 69.3$ ppm (dp, $^1J_{PH}$- 647 Hz, $^2J_{PH}$- 11 Hz). $^1$H NMR: $\delta = 1.16$ ppm (t, $^3J_{HH}$- 7 Hz, CH$_3$CH$_2$); $\delta = 3.98$ ppm, (m, $^3J_{HH}$- 7 Hz, CH$_3$CH$_2$); $\delta = 7.57$ ppm (d, $^1J_{HP}$- 647 Hz, P(S)H). $^{13}$C NMR: $\delta = 15.69$ ppm (qd, $^1J_{CH}$- 204 Hz, $^3J_{CP}$- 12 Hz, CH$_3$[PO]); $\delta = 61.78$ ppm (t, $^1J_{CH}$- 238 Hz).

PREPARATION OF Et$_3$TPFA (MICHAELIS-BECKER REACTION)

Finely divided sodium was suspended in dry benzene. The suspension was added to the solution of diethyl thiophosphite also dissolved in benzene. The mixture was heated to 50° C. for 2 h, then cooled to 5° C. with ice bath. Ethyl chloroformate dissolved in benzene was added drop-wise to the above mixture at room temperature. The mixture was heated to 50° C., for 3 h, then cooled to room temperature, and centrifuged. The clear resulting solution was washed with water, dried with MgSO$_4$, evaporated, and separated by fractional distillation in vacuo. The yield as 43%. Bp: 95°–96° C. (1.22 mm). IR. $^{31}$P NMR: $\delta = 61.4$ ppm, (P, $^3J_{PH}$- 10 Hz). $^1$H NMR: $\delta = 1.25$ ppm (m, $^3J_{HH}$- 7 Hz, CH$_3$), 9H; $\delta = 4.17$ ppm (m, $^3J_{HH}$- 7 Hz, CH$_2$), 6H. $^{13}$C NMR: $\delta = 13.7$ ppm (q, $^1J_{CH}$- 128 Hz, CH$_3$[CO]); $\delta = 15.8$ (qd, $^1J_{CH}$- 128 Hz, $^3J_{CP}$- 7 Hz, CH$_3$[PS]); $\delta = 62.1$ ppm (td, $^1J_{CH}$- 145 Hz, $^3J_{CP}$- 4 Hz, CH$_2$[CO]); $\delta = 64.2$ ppm (td, $^1J_{CH}$- 149 Hz, $^3J_{CP}$- 7 Hz, CH$_2$[PS]); $\delta = 167.3$ ppm (d, $^1J_{CP}$- 225 Hz, CO). Anal. Calculated for: C, 37.16; H, 6.68; S, 14.17. Found: C, 36.9; H, 6.62; S, 14.06.

PREPARATION OF METHYL (O,O-DIMETHYL) THIOPHOSPHONOFORMATE (ME$_3$TPFA) (PRESENT INVENTION METHODOLOGY)

LR and Me$_3$PFA were suspended in CH$_3$CN or THF and heated to 78° C. for 6 h and reaction was followed to TLC. The reaction mixture was then evaporated in vacuo; the components were separated by silica gel column using a mixture of hexane and ethyl acetate (6:1) as eluting solvents. The progress of the separation followed by TLC. The fractions were collected, combined, evaporated, and distilled in vacuo. The yield was 87%. Bp: 37°–38° C. (10 μm). IR. $^{31}$P NMR: $\delta = 64.8$ ppm (p, $^3J_{PH} = 14$ Hz). $^1$H NMR: $\delta = 3.81$ ppm (d, $^4J_{HP} = 1$, Hz$^6$, CH$_3$[CO]); $\delta = 3.83$ ppm (d, $^3J_{HP} = 14$ Hz, CH$_3$[PO]). $^{13}$C NMR: $\delta = 54.3$ ppm (qd, $^1J_{CH} = 150$ Hz, $^3J_{CP} = 7$ Hz, CH$_3$[PS]); $\delta = 52.7$ ppm (qd, $^1J_{CH} = 149$ Hz, $^3J_{CP} = 5$ Hz, CH$_3$[CO]); $\delta = 167.2$ ppm (d, $^1J_{CP} = 226$ Hz, CO). Mass. M/e: 184 (FW: 184.15). Anal. Calculated for: C, 26.09; H, 4.93; S, 17.41. Found: C, 26.23; H, 5.00; S, 17.82.

PREPARATION OF BENZYL (O,O-DIETHYL) THIOPHOSPHONOFORMATE (MICHAELIS-BECKER REACTION)

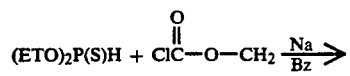

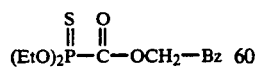

A finely divided sodium was suspended in dry benzene. The suspension as then added to a solution of diethyl thiophoshite in benzene. The mixture was heated to 50° C. for 1.5 h, then cooled to 5° C. in ice bath. Benzyl chloroformate dissolved in benzene was added drop-wise to the above mixture at room temperature. The resulting mixture was heated to 50° C. for 2.5 h, washed with H$_2$O, dried with MgSO$_4$, evaporated, and distilled in high vacuo. The yield was 48%.[1] Bp: 130°–132° C. (4 μm). IR. $^{31}$P NMR: $\delta = 61.2$ ppm (p, $^3J_{PH} = 10$ Hz). $^1$H NMR: $\delta = 1.196$ ppm (t, $^3J$HH$=7$ Hz), CH$_3$[PS]; $\delta = 4.132$ ppm (m, $^3J_{HH}=7$ Hz), CH$_2$[PS]; $\delta = 5.025$ ppm (s), CH$_2$[CO]; $\delta = 7.230$ ppm, C$_6$H$_5$[CO]. $^{13}$C NMR: $\delta = 16.0$ ppm (qd, $^1J_{CH}= 128$ Hz, $^3J_{CP}=7$ Hz, CH$_3$[PS]; $\delta = 64.6$ ppm (td, $^1J_{CH}=149$ Hz, $^3J_{CP}=7$ Hz, CH$_2$[PS]); $\delta = 69.5$ ppm (t, $^1J_{CH}=148$ Hz, CH$_2$[CO]); $\delta = 128.4$ ppm (d, $^1J_{CH}= 159$ Hz, C$_6$H$_5$[CO]); $\delta = 167.3$ ppm (d, $^1J_{CP}=224$ Hz, CO).

The compounds so produced were then subjected to ITMS hydrolysis as disclosed by Hutchinson et al. with the following results:

USING ME$_3$TPFA AS STARTING MATERIAL

On a small scale, the prior art method was successful at obtaining the desired product though it was expensive and time consuming. Utilizing classical aqueous TMS ester quenching conditions xcess ITMS was added to Me$_3$TPFA at room temperature with stirring under N$_2$. The mixture was heated to 110° C. (oil bath) for 5 h and the reaction progress followed by $^{31}$P NMR. Excess ITMS was removed under high vacuum and $^{31}$P and $^1$H NMR showed that the reaction was complete.

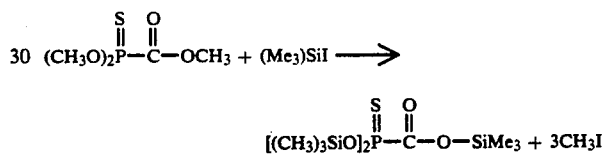

The residue was cooled in an ice bath. Cold water was added and the mixture stirred for 10 min. It was then titrated to pH 10.50 with NaOH solution. Excess solvent was evaporated by lyophilization. Methanol was added, and the mixture centrifuged. The product was oven-dried under vacuum producing a low yield of less than 10%.

When the hydrolyzed crude product was carefully analyzed, a decarboxilation reaction was also discovered:

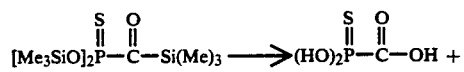

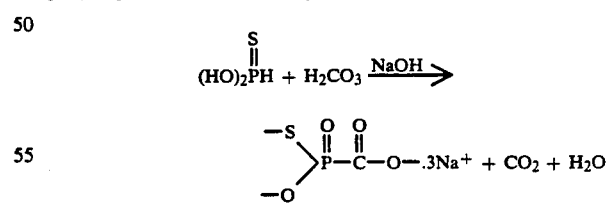

However, when increased amounts of Me$_3$TPFA (2 g) were used in the reaction, thereby necessitating longer reaction times (e.g., refluxing for 15 h) the reaction was not complete and the decomposition product quickly increased.

USING ET$_3$TPFA AS STARTING MATERIAL

Dealkylation of Et$_3$TPFA by treatment with ITMS was more difficult than that of Me$_3$TPFA. A mixture of Et$_3$TPFA and excess ITMS was refluxed at 120° C. (oil bath) and the reaction progress was followed by $^{31}$P NMR.

After 3 h, an intermediate was obtained:

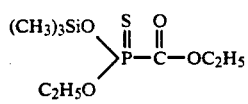

After 7 h, the didealkylation produced was obtained:

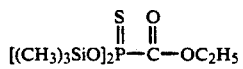

Accordingly, the reaction mechanism was presumed to be as follows:

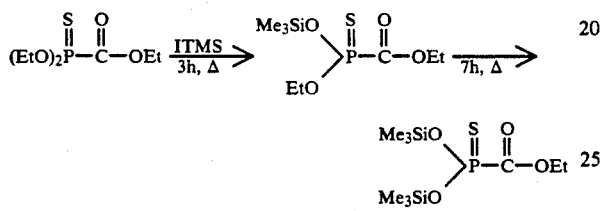

It should be noted that it was very difficult to remove the $C_2H_5$ from the carbonyl group because continued reflux with ITMS caused the side products to increase quickly. The reaction was repeated in the presence of an alkyl iodide in an attempt to use a Pishchimuka thionothiolo rearrangement to obtain the thiolo analogue prior to dealkylation-silylation with ITMS. Unfortunately, even after refluxing Et$_3$TPFA with 1-iodobutane in nitromethane for 44 h, only about 35% of thiolo analogue could be obtained ($^{31}$P, $\delta = 26.9$ ppm). Continued refluxing caused decomposition.

Further demonstrating the distinguishing features of the present invention over the teachings of the prior art, the following hydrolyzation methodology was developed in accordance with the teachings of the present invention in order to hydrolyze Me$_3$TPFA using ITMS while avoiding the problems of decarboxylation and decomposition associated with the prior art methodologies.

USING ME$_3$TPFA AS STARTING MATERIAL 2.5 mL (ca. 16 mmol) ITMS was added to 500 mg (2.72 mmol) of Me$_3$TPFA at room temperature with stirring under N$_2$. The mixture was heated to 115°-120° C. for 7 h and the reaction progress followed by $^{31}$P NMR. Excess ITMS was then removed under high vacuum (0.001 mm HG) at room temperature. The residue was cooled in an ice bath and was then added to 318 mg (3 mmol) of Na$_2$CO$_3$ in 2 mL water and dissolved with stirring. The mixture was adjusted to pH 10.5 using 3N NaOH solution (approximately 0.5 mL). On addition of 35 mL of methanol, a precipitate formed which was centrifuged 10 min. and dried in a vacuum oven (<1 mm Hg at 50° C.), neutralized to pH 4.5 with 3N HCl (approximately 4 mL), then readjusted to pH 10.5 with 3N NaOH (ca. 0.5 mL). Reprecipitation with 35 mL of methanol, centrifugation as above, and oven drying in vacuo (<1 mm Hg, 50° C.) gave a white precipitate. This was redissolved in 3 mL of water, and the same procedure repeated three times. After drying (<1 mm Hg, 55° C, 6 h), 243.9 mg (43% yield) Na$_3$T-PFA, (white powder) was obtained. $^{31}$P NMR: $\delta = 37.7$ ppm (s). $^1$H NMR: no resonances except HDO. $^{13}$C NMR: $\delta = 183.3$ ppm (d, $^1J_{CP} = 181$ Hz, CO).

Accordingly, from the foregoing it will be readily apparent to those skilled in the art that the prior art method of Hutchinson et al., while marginally successful at producing some intermediate compounds, does not produced TPFA or its addition salts. Apparently, the conversion of the phosphonate to the thiophosphonate compound interferes with the reactivity of ITMS. As a result, mixtures are produced by the prior art rather than pure compounds. As those skilled in the art will also appreciate, the significant questions raised as to the results of the reported synthesis by Hutchinson et al. also raise doubts as to the reproducability or veracity of any antiviral data that may have been published with respect to PFA or TPFA.

In contrast, the method of the present invention is highly successful at inexpensively producing large yields of pure TPFA thereby enabling its antiviral properties to be properly ascertained. More particularly, as shown in the following, non-limiting examples, in accordance with the teachings of the present invention, TPFA is unexpectedly effective against both HIV and HIV reverse transcriptase.

Inhibition of a variety of viral enzymes was measured in order to determine the ID$_{50}$ or Inhibitory Dosage 50 of TPFA versus its phosphonate analogue PFA utilizing the following protocol.

PREPARATION OF DNA POLYMERASES

Viral DNA polymerases (HSV-1, HSV-2, EBV) were purified by previously published methods (Derce, D., K. F. Bastow, and Y. C. Cheng (1982) J. Boil. Chem. 257:10251-10260; Ostrander, M., and Y. C. Cheng (1980) Biochim. Biophys. Acta 609:232-245; Tan, R. S., A. Datta, and Y. C. Cheng (1982) J. Virol. 44:893-899). These procedures generally included sequential chromatography on DEAE-cellulose. HIV reverse transcriptase was purified by antibody affinity column chromatography as described (Starnes, M. C., and Y. C. Cheng (1989) J. Biol. Chem. 264:7073-7077). The purified enzymes were dialyzed against and stored in 50 mM Tris-HCl (pH 7.5) containing 1 mM each of DTT, EDTA and PMSF plus 30% glycerol. Mammalian DNA polymerases alpha, beta, gamma, and delta were partially purified from K562 celles (chronic myelogenous leukemia tissue culture line). Briefly, washed cell pellets were extracted and passed through DEAE-cellulose in the presence of 300 mM KPO$_4$ (pH 7.5) as previously described (Starnes, M. C., and Y. C. Cheng (1987) J. Biol. Chem 262:988-991) to remove DNA. The column flow-through fractions were dialyzed against buffer which contained 50 mM Tris-HCl (pH 7.5), and fractionated on a single-stranded DNA-cellulose column with a 0-1M KCl gradient. Mammalian polymerases (peak fractions) were completely separated from each other and exhibited the typical inhibitor profile and associated enzyme activities for each enzyme (effect of aphidicolin, dideoxynucleotides, butyiphenyl-dGTP, and ionic strength, presence of primase and reverse transcriptase activity).

HIV-1 REVERSE TRANSCRIPTASE ASSAYS

Standard assays were run at 37° C. and contained: 50 mM Tris, pH 8.0, 0.5 mM DTT, 8 mM MgCl$_2$, 100 $\mu$g/mL BSA, 150 $\mu$g/mL gapped calf thymus DNA, 100 μM each dATP, dCTP, dGPT, 10 μM [³H]-dTTP, and 1-5 μL enzyme in a final volume of 50 μL. Modified assays for pH dependence inhibition studies with PFA (1) and α—oxo phosphonates (4 and 5) contained 50 mM Hepes, pH 8.2-6.5, 8 mM $MgCl_2$, 100 mM KCl, 100 μg/ml BSA, 0.5 $A_{260}$ units/ml of poly(rA).(dT)$_{10}$, 100 μM [³H]dTTP, and 1-5 μL enzyme in a final volume of 50 μL. Samples were processed as described above.

The results of these assays were tabulated as follows:

TABLE I

| Virus | Viral Polymerase Inhibition $ID_{50}$ (μM)* | |
|---|---|---|
| | TPFA | PFA |
| HIV-1 | 1 | 0.7 |
| HSV-1 | 11.8 | 0.7 |
| HSV-2 | 11.3 | 0.7 |
| EBV | 70 | 1 |
| HV-6 | 70 | 1 |

*All assays with "activated" DNA.

As those skilled in the art will appreciate, from the foregoing the $ID_{50}$ with respect to HIV for TPFA is essentially identical to that for PFA. This is in startling contrast to the effectiveness of TPFA relative to PFA with respect to the other virus enzymes tested. As shown in Table I TPFA is fifteen to twenty times less effective than PFA with respect to Herpes Simplex virus Type I and II and more than seventy times less effective against Epstein-Barr virus and Herpes Virus 6. Yet TPFA is equally effective against HIV. Thus, as will be appreciated by those skilled in the art, while the antiviral inhibitory activity of TPFA is completely unpredictable it is also surprisingly effective against HIV.

Moreover, the test results shown in Table I indicate that the previously reported inhibitory effects of TPFA and PFA are incorrect. More specifically, Hutchinson et al. reported relative $ID_{50}$ values for PFA and TPFA with respect to HSV-1 of, respectively, 12 and 9. In that the pure compounds of the present invention tested in Table I show a difference in inhibition activity with respect to HSV-1 on the order of a factor of 12 between TPFA and PFA, it would appear that Hutchinson et al. who report an essentially identical activity between the two compounds were most likely measuring mixtures rather than pure compounds. Thus, because of the prior art difficulties in producing TPFA, it is clear that the previously reported antiviral activities of TPFA are incorrect.

In accordance with the teaching of the present invention similar enzyme inhibition assays wee also conducted with respect to mammalian enzymes, more particularly, human DNA polymerase. The results of these tests are tabulated as follows:

TABLE II

| Pol | Human DNA Polymerase Inhibition % Control at 100 μM ± S.D. ($ID_{50}$. μM)$^a$ | |
|---|---|---|
| | TPFA | PFA |
| α | 72 ± 3 (>100) | 16 ± 2 (31) |
| β | 91 ± 4 (>100) | 89 ± 8 (>100) |
| γ | 75 ± 3 (>100) | 55 ± 5 (>100) |
| δ | 69 ± 6 (>100) | 36 ± 3 (71) |

$^a$All assays with "activated" DNA.

As shown in Table II the estimated $ID_{50}$ of TPFA with respect to these mammalian enzymes is significantly higher than that for PFA, especially with respect to human DNA polymerase-Alpha, the most important DNA polymerase in this comparison. Even more significantly, TPFA is greater than 100 fold less active against the human enzyme than it is against the HIV enzyme tested in Table I. Accordingly, the therapeutic index for TPFA is relatively high. In fact, as shown in Tables I and II the therapeutic index for TPFA with respect to HIV enzyme and human enzyme is such that TPFA is, at a minimum, three times less toxic to the human enzyme than PFA yet is equally effective against the viral enzyme.

In addition to testing the activity of TPFA against HIV enzyme, the activity against the virus itself was also determined in accordance with the following protocol. The experimental protocol involved incubation of H9 lymphocytes (3.5×10⁶ cells/ml) in the presence or absence of HIV-1 (HTLV-IIIB) for one hour at 37° C. Cells were washed thoroughly to remove unabsorbed virions and re-suspended at 4×10⁵ cells/ml in culture medium. Aliquots (1 ml) were placed in wells of 24 well culture plates containing any equal volume of test compound (diluted in culture medium). After incubation for three days at 37° C., cell density of uninfected cultures was determined to assess toxicity of the test compound. A p24 antigen capture was used to determine the level of HIV infection in HIV treated cultures. The ability of test compounds to inhibit HIV replication was measured at different concentrations relative to infected, untreated cultures. Test compounds were considered to be active if p24 levels were <70% of infected, untreated cultures. Cytotoxicity in uninfected H9 cells was not detected.

The results from this experimental data were tabulated in the following table:

TABLE III

| | HIV Inhibition In Cell Culture$^a$ | | | | |
|---|---|---|---|---|---|
| Drug Type | Drug Conc. (μg/mL) | Cell Survival (%) | Toxicity | p24 Ave (%) | Inhibition Score$^b$ |
| PFA | 120 | 102 | non-T | −2 | *** |
| | 30 | 92 | non-T | 10 | *** |
| | 7.5 | 96 | non-T | 35 | ** |
| | 1.9 | 98 | non-T | 88 | |
| TPFA | 200 | 84 | non-T | −3 | *** |
| | 50 | 93 | non-T | 0 | *** |
| | 10 | 104 | non-T | 35 | ** |
| | 2 | 110 | non-T | 90 | |
| | 0.5 | 113 | non-T | 117 | |
| | 0.1 | 113 | non-T | 139 | |

$^a$p24 antigen capture assay.
$^b$*, strong; , moderate; *, weak.
REMARKS:
Control untreated H9 cell count—1.07 million.
Control infected H9 p24 = 357 μg/mL
Drug concentration μg/mL
Toxic:
"non-T" >70% cell survival
"T" <70% cell survival
Score:
* 50–69% control p24
** 25–49% control p24
*** <25% control p24

As those skilled in the art will appreciate, in Table III the lower the value of p24 the more active the compound is at inhibiting HIV. As shown in Table III, TPFA is as effective at inhibiting HIV at 50 μg/mL as PFA is at 120 μg/mL. Coupling these results with the previously discussed therapeutic index of TPFA, it becomes abundantly clear that TPFA is unexpectly superior to its phosphonate analogue PFA with respect to inhibition of HIV. What is more, as those skilled in the art will also appreciate, there is good reason to believe that TPFA will be significantly less toxic in treating mammals as well as more effective. For example, TPFA exhibits a lower molecular polarity enhancing its water solubility and cell penetration properties. Thus, unlike PFA which may crystalize in the kidneys causing a toxic reaction, the higher solubility compound TPFA is less likely to crystalize and cause such side effects. Additionally, because the thiophosphonate compound is less like a phosphate compound it should exhibit a reduced tendency to deposit in bone.

Moreover, as those skilled in the art will also appreciate, TPFA and/or its addition salts can be administered to mammals including humans in an effective amount as determined by clinical trials. The compound may be administered orally, parenterally, topically or by other standard administration routes. Additionally, the compound can include a pharmaceutically acceptable carrier such as the normally acceptable additives, excipients, and the like and may also be combined with other bioreactive compounds such as AZT, DDC, DDI and antibiotics.

An additional advantage of TPFA over PFA is that the ultraviolet spectrum of TPFA is about ten times more intense than that of PFA and is easier to detect. The presence of sulfur in TPFA tends to shift the ultraviolet absorption towards the red-end of the spectrum making it more convenient to measure. As a result, the TPFA produced in accordance with the teachings of the present invention has additional analytical benefits for chemical research.

Having thus described exemplary embodiments of the present invention, it should be noted by those skilled in the art that the within disclosures are exemplary only and that various other alternatives, adaptations and modifications may be made within the scope of the present invention. For example, solvents other than acetonitrile or toluene may be utilized as well as other inert gases in place of the argon disclosed and claimed. Additionally, other phosphonate starting materials may be utilized than those disclosed in the foregoing non-limiting examples. Accordingly, the present invention is not limited to the specific embodiments as illustrated herein, but is only limited by the following claims.

What is claimed is:

1. A method for the conversion of trimethyl phosphonoformate into trimethyl thionophosphonoformate, said method comprising the steps of:
    forming a reaction mixture of trimethyl phosphonoformate, an effective amount of Lawesson's reagent and polar, aprotic solvent; and
    heating said reaction mixture until conversion is substantially complete.

2. The method of claim 1 further comprising the additional step of separating said trimethyl thiophosphonoformate from said reaction mixture.

3. The method of claim 1 wherein said trimethyl thiophosphonoformate is separated from said reaction mixture through distillation.

4. The method of claim 1 wherein said polar aprotic solvent is acetonitrile.

5. The method of claim 1 wherein said reaction mixture is heated under an inert, anhydrous atmosphere.

6. A method of treating a human infected with the human immunodeficiency virus (HIV) to inhibit HIV activity comprising the administration of a pharmaceutically effective amount of thiophosphonoformic acid (TPFA) or a pharmaceutically acceptable salt thereof.

7. A method of treating a human infected with the human immunodeficiency virus (HIV) to inhibit HIV activity comprising the administration of a pharmaceutical composition comprising an effective amount of thiophosphonoformic acid (TPFA) or a pharmaceutically acceptable salt thereof and a pharmaceutically acceptable carrier.

* * * * *